(12) United States Patent
Eastman et al.

(10) Patent No.: US 9,700,241 B2
(45) Date of Patent: Jul. 11, 2017

(54) GAIT ANALYSIS SYSTEM AND METHOD

(71) Applicant: Under Armour, Inc., Baltimore, MD (US)

(72) Inventors: Kyler Eastman, Austin, TX (US); Kevin Callahan, Austin, TX (US); Robin Thurston, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 659 days.

(21) Appl. No.: 14/097,082

(22) Filed: Dec. 4, 2013

(65) Prior Publication Data

US 2014/0156215 A1 Jun. 5, 2014

Related U.S. Application Data

(60) Provisional application No. 61/733,312, filed on Dec. 4, 2012.

(51) Int. Cl.
*A61B 5/11* (2006.01)
*A61B 5/00* (2006.01)

(52) U.S. Cl.
CPC ............ *A61B 5/112* (2013.01); *A61B 5/0022* (2013.01); *A61B 5/1112* (2013.01); *A61B 5/6898* (2013.01)

(58) Field of Classification Search
None
See application file for complete search history.

(56) References Cited

U.S. PATENT DOCUMENTS

| | | | |
|---|---|---|---|
| 7,080,065 B1 | 7/2006 | Kothuri et al. | |
| 7,092,846 B2 | 8/2006 | Vock et al. | |
| 7,647,196 B2 * | 1/2010 | Kahn .................. | A61B 5/0022 702/142 |
| 7,881,902 B1 | 2/2011 | Kahn et al. | |
| 7,901,292 B1 | 3/2011 | Uhlir et al. | |
| 8,060,337 B2 | 11/2011 | Kulach et al. | |
| 8,112,251 B2 | 2/2012 | Case et al. | |
| 8,364,389 B2 | 1/2013 | Dorogusker et al. | |

(Continued)

OTHER PUBLICATIONS

Office Action for U.S. Appl. No. 13/440,799, mailed May 4, 2012, 23 pgs.

(Continued)

*Primary Examiner* — An Do
*Assistant Examiner* — Renee I Wilson

(57) ABSTRACT

A system for gait analysis may include a mobile data recording device configured to record accelerations associated with user motion and a data processing device in communication with the mobile data recording device. The data processing device can be configured to receive acceleration data from the mobile data recording device and process the acceleration data to extract stride data sequences from the acceleration data through use of bounding boxes on one or more points of the acceleration data. Each of the stride data sequences comprising data for a corresponding stride. The bounding boxes may define time and acceleration bounds. The data processing system may further determine one or more stride metrics. According to one embodiment, the data recording device may be a smartphone or other device having an accelerometer with a limited range that is inadequate to capture the full range of accelerations experienced by a runner.

21 Claims, 12 Drawing Sheets

(56) References Cited

U.S. PATENT DOCUMENTS

| | | | |
|---|---|---|---|
| 8,374,888 | B2 | 2/2013 | Earles et al. |
| 8,438,038 | B2 | 5/2013 | Cosentino et al. |
| 8,446,275 | B2 | 5/2013 | Utter, II |
| 8,983,637 | B2 | 3/2015 | Glode et al. |
| 2002/0040601 | A1 | 4/2002 | Fyfe et al. |
| 2005/0288154 | A1 | 12/2005 | Lee et al. |
| 2007/0021979 | A1 | 1/2007 | Cosentino et al. |
| 2007/0062279 | A1 | 3/2007 | Chan et al. |
| 2007/0208544 | A1 | 9/2007 | Kulach et al. |
| 2008/0096726 | A1 | 4/2008 | Riley et al. |
| 2009/0076903 | A1 | 3/2009 | Schwarzberg et al. |
| 2009/0089262 | A1 | 4/2009 | Cheng et al. |
| 2009/0150178 | A1 | 6/2009 | Sutton et al. |
| 2009/0204597 | A1 | 8/2009 | Mani et al. |
| 2011/0032105 | A1 | 2/2011 | Hoffman et al. |
| 2011/0179458 | A1 | 7/2011 | Eisner |
| 2011/0197157 | A1 | 8/2011 | Hoffman et al. |
| 2011/0289443 | A1 | 11/2011 | Heaven et al. |
| 2012/0028761 | A1 | 2/2012 | Dorogusker et al. |
| 2012/0116550 | A1 | 5/2012 | Hoffman et al. |
| 2012/0239173 | A1 | 9/2012 | Laikari et al. |
| 2012/0253234 | A1 | 10/2012 | Yang et al. |
| 2012/0253488 | A1 | 10/2012 | Shaw et al. |
| 2012/0254212 | A1 | 10/2012 | Shaw et al. |
| 2012/0254226 | A1 | 10/2012 | Shaw et al. |
| 2013/0090749 | A1 | 4/2013 | Oswald et al. |
| 2013/0158686 | A1 | 6/2013 | Zhang et al. |
| 2013/0190657 | A1* | 7/2013 | Flaction .............. A61B 5/1038 600/595 |
| 2013/0190903 | A1* | 7/2013 | Balakrishnan ....... A61B 5/7246 700/91 |
| 2014/0018705 | A1* | 1/2014 | Wang .................... A61B 5/112 600/595 |
| 2014/0031959 | A1 | 1/2014 | Glode et al. |
| 2014/0122494 | A1 | 5/2014 | Thurston et al. |

OTHER PUBLICATIONS

Office Action for U.S. Appl. No. 13/077,410, mailed Jun. 11, 2012, 23 pgs.

Amendment for U.S. Appl. No. 13/440,799, dated Jul. 26, 2012, 8 pgs.

Amendment for U.S. Appl. No. 13/077,410, dated Aug. 29, 2012, 8 pgs.

Office Action for U.S. Appl. No. 13/440,799, mailed Dec. 4, 2012, 29 pgs.

Office Action for U.S. Appl. No. 13/077,410, mailed Dec. 6, 2012, 31 pgs.

Veltkamp, Remco C., Shape Matching: Similarity Measures and Algorithms, Jan. 2001, No. UU-CS-2001-03, 16 pgs., Utrecht University, Utrecht, The Netherlands.

Chapman, Robert F. et al., Ground Contact Time as an Indicator of Metabolic Cost in Elite Distance Runners, Medicine & Science in Sports & Exercise, May 2012, vol. 44, pp. 917-925, Journal of the American College of Sports Medicine, Indianapolis, IN (http://www.acsm.org).

Snyder, Kristine L. et al., Energetically optimal stride frequency in running: the effects of incline and decline, The Journal of Experimental Biology 214, pp. 2089-2095, published Jun. 2011, The Company of Biologists Limited, Cambridge, UK.

Milner, Clare E. et al., Biomechical Factors Associated with Tibial Stress Fracture in Female Runners, Medicine & Science in Sports & Exercise, 2006, vol. 38, pp. 323-328, Journal of the American College of Sports Medicine, Indianapolis, IN (http://www.acsm.org).

Office Action for U.S. Appl. No. 13/561,107, mailed Oct. 9, 2013, 9 pgs.

Office Action for U.S. Appl. No. 13/561,107, mailed May 29, 2014, 9 pgs.

Advisory Action for U.S. Appl. No. 13/561,107, mailed Aug. 1, 2014, 3 pgs.

Notice of Allowance for U.S. Appl. No. 13/561,107, mailed Nov. 17, 2014, 4 pgs.

International Preliminary Report on Patentability (Ch. I) for International Patent No. PCT/US2013/067834, issued May 5, 2015, 6 pgs.

International Search Report and the Written Opinion issued for PCT Application No. PCT/US2013/073178, mailed May 16, 2014, 8 pages.

Neil Zhao, "Full-Featured Pedometer Design Realized with 3-Axis Digital Accelerometer," Analog Dialogue 44-06, Jun. 2010, 5 pgs.

Toshiki Iso et al., "Gait Analyzer based on a Cell Phone with a Single Three-Axis Accelerometer," Mobile HCI'06, Sep. 12-15, 2006, pp. 141-144, Helsinki, Finland (ACM 1-59593-390-5).

Martin Eriksson et al., "Wireless Vertical Displacement Measurement During Running Using an Accelerometer and a Mobile Phone," Biomechanics in Sports, Portuguese Journal of Sports Sciences 11 (Suppl. 2), 2011, pp. 863-866, Porto, Portugal.

Elena Bergamini, et al., "Estimation of Temporal Parameters During Sprint Running Using a Trunk-Mounted Inertial Measurement Unit," Journal of Biomechanics (2012), doi:10.1015/j.jbiomech.2011.12.020, 4 pgs.

"What are Segments?," Feb. 3, 2013, 1 pg., Strava, San Francisco, CA, retrieved on Oct. 15, 2013 from <<https://strava.zendesk.com/entries/20945952-what-are-segments>>.

"Segments—A New Tool for Analysis and Competition," retrieved on Oct. 15, 2013, 12 pgs., from <<http://ridewithgps.com/segments/help>>.

International Search Report and the Written Opinion issued for PCT Application No. PCT/US2013/067834, mailed Mar. 28, 2014, 8 pages.

Office Action for U.S. Appl. No. 14/068,972, mailed Sep. 18, 2015, 19 pgs.

* cited by examiner

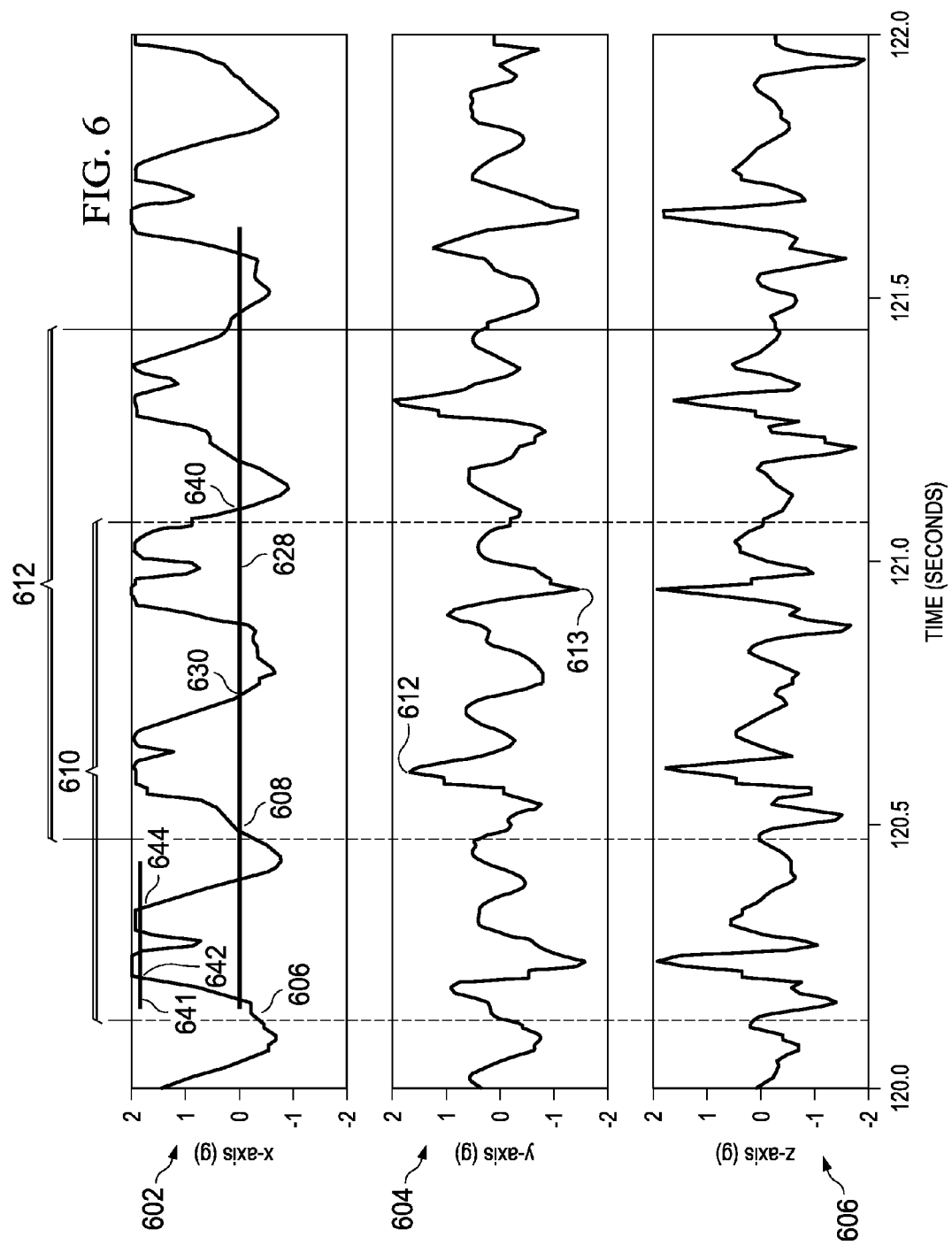

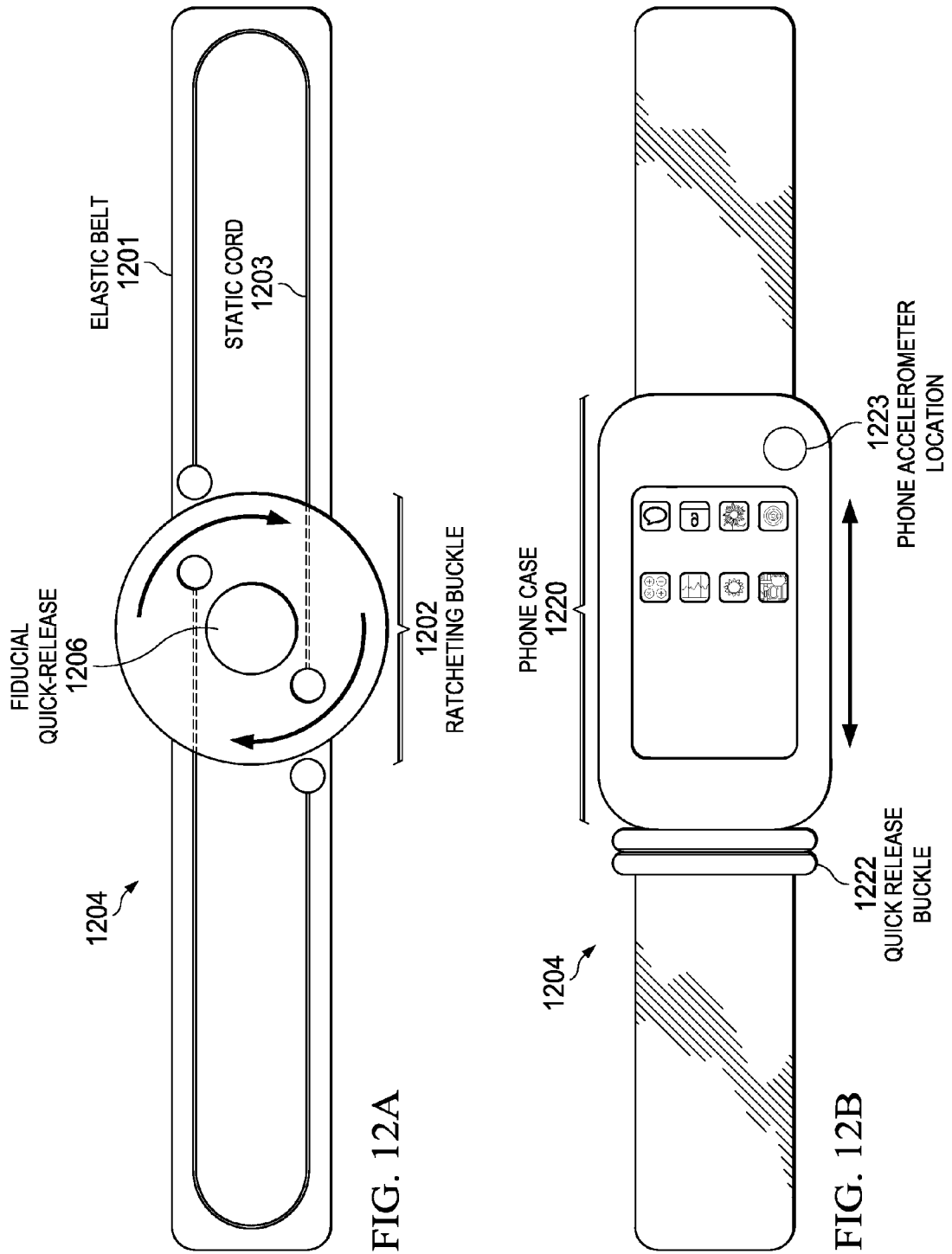

GAIT ANALYSIS SYSTEM AND METHOD

CROSS-REFERENCE TO RELATED APPLICATION(S)

This application claims the benefit of U.S. Provisional Application Ser. No. 61/733,312, entitled "Gait Analysis System and Method," by Eastman et al., filed Dec. 4, 2012, which is fully incorporated by reference in its entirety as if fully set forth herein.

TECHNICAL FIELD

This disclosure relates generally to the field of motion analysis. In particular, some embodiments relate to gaining information metrics related to biological motion, such as gait.

BACKGROUND

The sport of running has become increasingly popular. The number of finishers of marathons and half-marathons has more than doubled over the past ten years. As it has become increasingly clear that a runner's technique or form can affect performance and contribute to or prevent injury, gait analysis has increasingly become an area of interest.

Traditionally, gait analysis has been limited merely to determining whether a runner under-pronates or over-pronates, and selecting the appropriate shoes to compensate therefor. However, as scientific studies of techniques practiced by competitive runners have become more widely known, the importance of factors such as stride rate, contact time, and bounce has become clear. Accordingly, it has become increasingly desirable for runners to be able to obtain such information in real time from real runs on courses that the runners traverse every day.

Sensor devices have been specifically designed to gain informative metrics about biological motion, particularly bipedal motion (walking or running). Devices for obtaining these metrics have included both Global Positioning System (GPS) and motion sensors. However, these are typically specialized devices, often using either GPS or motion, but not both. Furthermore, the specialized nature of these devices require a high amount of engineering development to employ sensitive detectors, which requires a high amount of power consumption, and yet still maintain a low weight for the overall product, enough to be practical or unobtrusive while running.

SUMMARY OF THE DISCLOSURE

Embodiments disclosed herein provide a system, method, and computer program product for gait analysis. In some embodiments, a gait-analysis method may be embodied in a computer program product comprising at least one non-transitory computer readable medium storing instructions translatable by at least one processor to perform the method. In some embodiments, a gait analysis system may comprise software and hardware, including the at least one non-transitory computer readable medium.

A system for gait analysis may include a mobile data recording device configured to record accelerations associated with user motion and a data processing device in communication with the mobile data recording device. The data processing device can be configured to receive acceleration data from the mobile data recording device and process the acceleration data to extract stride data sequences from the acceleration data through use of bounding boxes on one or more points of the acceleration data. Each of the stride data sequences can comprise data for a corresponding stride. The bounding boxes, according to one embodiment, may define time and acceleration bounds. The data processing system may further determine one or more stride metrics.

A method for gait analysis may comprise recording acceleration data associated with a user's gait collected during a run at a mobile data recording device. The method may further comprise processing the acceleration data to extract stride data sequences from the acceleration data corresponding to the run through use of bounding boxes on one or more points of the acceleration data. The bounding boxes may define time and acceleration bounds. Each of the stride data sequences may comprise data corresponding to a stride. The method can further include determining one or more stride metrics utilizing the stride data sequences and providing the one or more stride metrics for display on a display device.

Another embodiment can include a computer program product comprising a non-transitory computer readable medium storing instructions for implementing a method for gait analysis. The method may comprise receiving acceleration data collected by a mobile data recording device carried by a user, extracting stride data sequences from the acceleration data through use of bounding boxes on one or more points of the acceleration data, determining one or more stride metrics utilizing the stride data sequences and providing the one or more stride metrics for display by the data recording device. The bounding boxes may define time and acceleration bounds and each of the stride data sequences may comprise data for a corresponding stride.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The drawings accompanying and forming part of this specification are included to depict certain aspects of the disclosure. It should be noted that the features illustrated in the drawings are not necessarily drawn to scale. A more complete understanding of the disclosure and the advantages thereof may be acquired by referring to the following description, taken in conjunction with the accompanying drawings in which like reference numbers indicate like features and wherein:

FIG. 6 illustrates exemplary data for x, y, and z axes.

FIG. 12A and FIG. 12B illustrate an example belt for device positioning according to embodiments.

DETAILED DESCRIPTION

Figure 1:
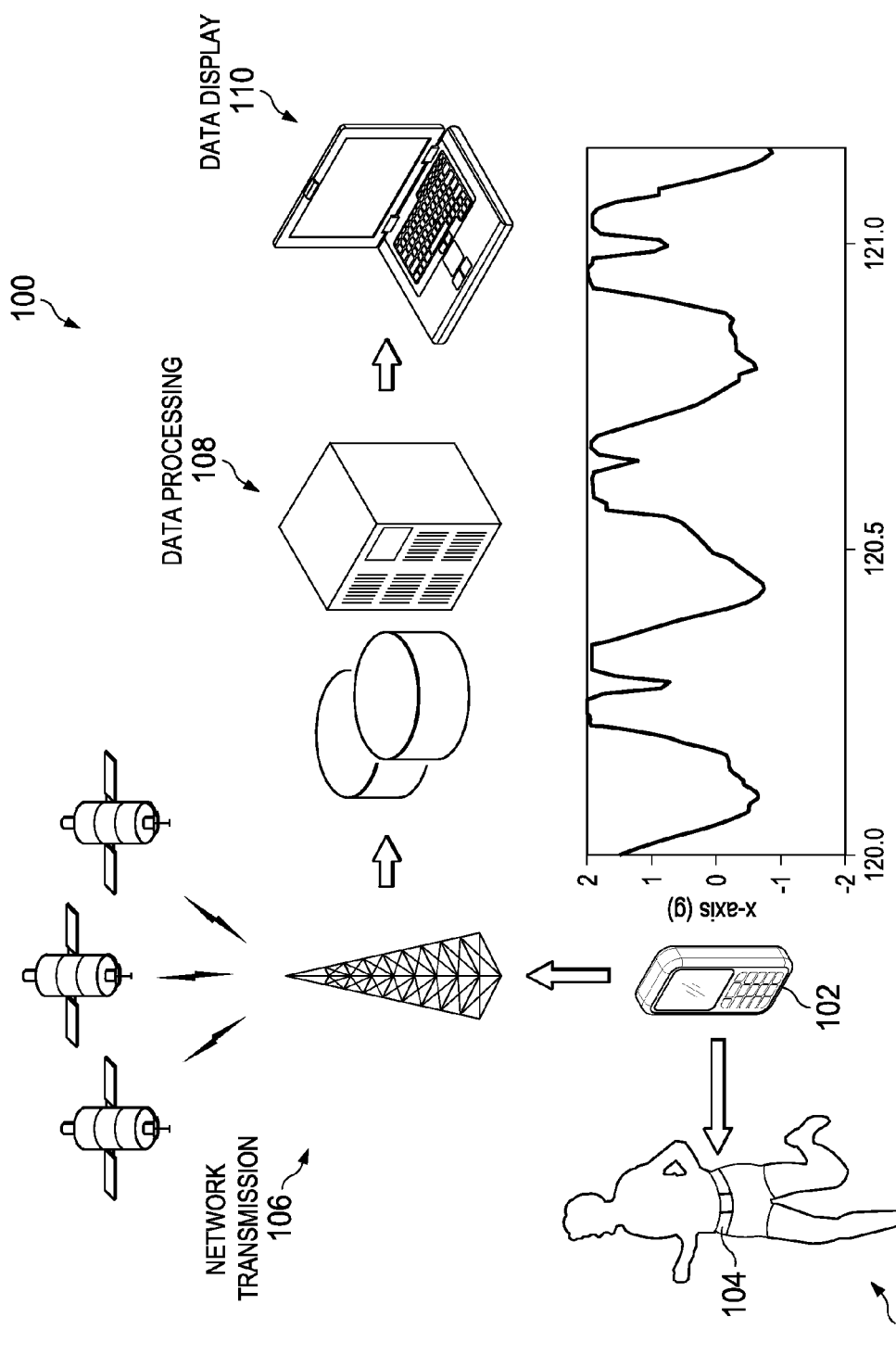
FIG. 1 is a diagram illustrating a gait analysis system according to embodiments.

The disclosure and various features and advantageous details thereof are explained more fully with reference to the exemplary, and therefore non-limiting, embodiments illustrated in the accompanying drawings and detailed in the following description. Descriptions of known programming techniques, computer software, hardware, operating platforms and protocols may be omitted so as not to unnecessarily obscure the disclosure in detail. It should be understood, however, that the detailed description and the specific examples, while indicating the preferred embodiments, are given by way of illustration only and not by way of limitation. Thus, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like. Various substitutions, modifications, additions and/or rearrangements within the spirit and/or scope of the underlying inventive concept will become apparent to those skilled in the art from this disclosure.

Embodiments described herein provide systems and methods for analyzing the gait of a runner. A system can use a variety of sensors to detect the motion and other characteristics of the runner. One advantage of embodiments of the present disclosure is that they can utilize sensors, such as the accelerometers within cellular telephones or smartphones, which are not specialized for detecting biological movement.

For purposes of discussion, a "stride" is a single coordinated movement of the two legs of a person, completed when the legs return to their initial relative position (i.e., a complete gait cycle, defined by the complete cycle of a reference limb, typically comprising two steps); a "stride signature" is the series of fluctuations the sensor data goes through during a complete stride; "contact time" is a measure of the amount of time each foot is on the ground. Contact time is usually expressed in milliseconds, and can range from 100-2000; "stride rate" is the number of complete strides in a given amount of time; a "sequence" is a series of digitally encoded signals (e.g., of a particular sensor parameter) that captures one or more stride signatures or portions thereof. For example, as a person runs a single stride, an accelerometer will record a particular pattern. This pattern repeats, with variations, for every stride.

Turning now to the drawings and with particular attention to FIG. 1, a diagram of a system 100 in accordance with embodiments is shown. As will be discussed in greater detail below, a mobile data recording device 102 may be affixed to a runner 101 using a harness 104, such as a belt or other harness, or other affixing mechanism. Data recording device 102 can include an internal or external accelerometer to measure acceleration in one or more axes. Data recording device 102 may also include one or more positioning systems, such as a GPS chip, gyroscope, and other sensors. Processing of data collected by data recording device 102 can occur at the data recording device 102, at another device, or a combination thereof.

In some embodiments, the data recording device 102 may be a cellular telephone, or smartphone, including an accelerometer. Example smartphones include the iPhone, available from Apple, Inc., of Cupertino, Calif.; various phones running the Android operating system or other mobile operation system, available from a variety of manufacturers; and other phones. Other computing devices having internal or external accelerometers, GPS (or other positioning) sensors or other sensors may also be used. Such devices may be configured for sampling data at a sufficiently high rate to capture the movements of each stride through changes in acceleration and rotation. Some suitable accelerometers for a device include, for example, an LIS302DL manufactured by ST Microelectronics of Geneva, Switzerland, or an ADXL321 manufactured by Analog Devices of Norwood, Mass.

Accelerometers in cell-phones or other devices, coupled with the ability to track speed and distance, provide the opportunity to derive gait characteristics that are important to athletes and can reduce injury and enhance performance. Most runners experience between greater than 5 G of vertical acceleration when running. However, some accelerometers fail to meet the requirements for direct measurement of these parameters. For example, some phones have accelerometers that fail to record G forces greater than a certain amount (e.g., 2 Gs, 9.8 m/s/s) and, accordingly, fail to record various aspects of a runner's gait. However, embodiments are able to compensate for these limitations in off-the-shelf or other limited accelerometers.

In some embodiments, some stride metrics, such as stride rate, may be computed from the raw accelerometer data, in real-time, at the data recording device 102. Other stride metrics may be more preferably processed on a remote server or computer (e.g., data processing device 108, user device 110, or another device). This can be for a variety of reasons, such as requiring additional computing power, access to a database of stride metrics from past runs of other users, and enhanced visualization capabilities.

Raw sensor data from the data recording device 102 may be compressed and transmitted via a network 106, such as the Internet, cellular network or other wired or wireless communication network or networks. In some embodiments, the data may be provided in real-time or near real-time over a wireless network as the user runs. In other embodiments, the data may be provided in a batch process at the end of run by data recording device 102, a user's laptop or desktop computer or according to another scheme.

The data may be provided to one or more data processing devices 108. Such data processing devices 108 may comprise one or more computers configured to analyze the raw data, such as accelerometer, GPS data or other data. The processed data may then be provided for display to one or more user devices 110. User devices 110 may be, e.g., laptop or desktop computers, tablet computers, or cellular telephones running applications configured to suitably display such analyzed data. In some embodiments, the user device 110 may be the same as the data recording device 102. Further, in some embodiments, the data processing functions of the data processing device 108 may be handled by either or both of the data recording device 102 and the user device 110. Thus, while a specific architecture is illustrated, other architectures may be used.

Figure 2:
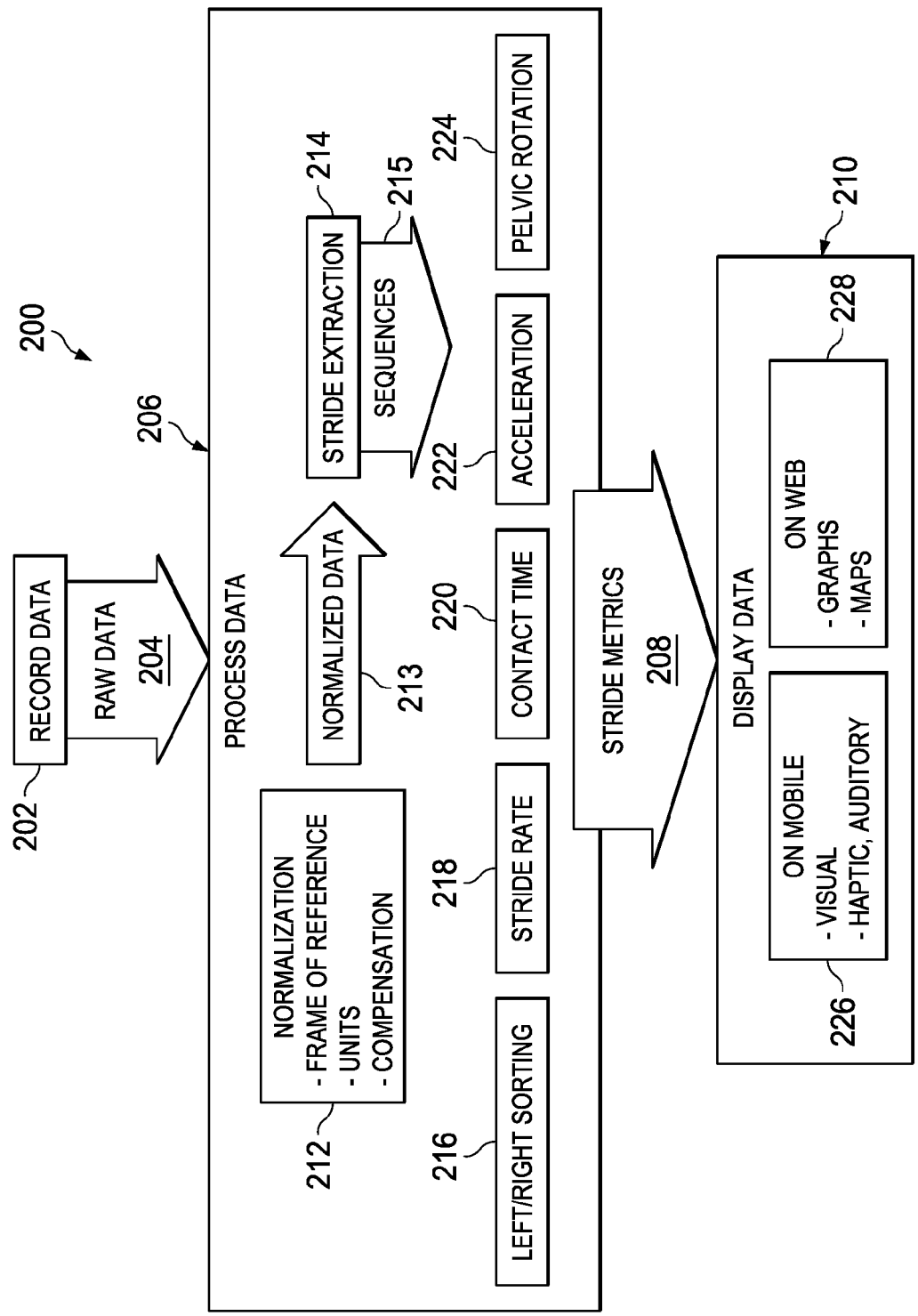
FIG. 2 illustrates a system process flow according to embodiments.

FIG. 2 is a functional block diagram illustrating one embodiment of flow through a gait analysis system. As will be discussed in greater detail below, the system flow 200 includes a data recording component 202, a data processing component 206, and a data display component 210. Data recording component 202 may be implemented using the data recording device (e.g., data recording device 102 of FIG. 1), preferably a smartphone. The data processing component 206 and display component 208 may be implemented using the data recording device 102 and/or one or more of the servers or user computers, as discussed above.

Data recording component 210 can record vertical acceleration data. Data recording component 210 may also record lateral acceleration (side-to-side) and longitudinal acceleration (forward, backward). Data recording component 210 may also record GPS readings, gyroscope readings, temperature, altitude, or other parameters measured by a data recording device.

Raw data 204 can be provided to processing component 206 for processing. Processing component 206 can implement any number of steps. According to an embodiment, processing component 206 can include a normalization component 212, a stride extraction component 214, left-right sorting component 216, stride rate component 218, contact time component 220, acceleration component 222, and pelvic rotation component 224. Stride metrics 208 can be provided to a display component 210 that can process the stride metrics 208 for display on a variety of devices including, but not limited to, mobile devices and/or over the World Wide Web.

According to some embodiments, the data can be normalized in a normalization component 212. Normalization can include a number of steps, such as potentially changing the frame of reference; converting the data into standard units; compensating for abnormal placement of the data recording device 102 or other normalization.

Normalized data 213 may be provided to stride extraction component 214. The stride extraction component 214 converts the continuous recordings of the sensors from the running activity into arrays of segments of data sequences 215. In one embodiment, each sequence 215 includes the corresponding sensor data for a particular stride (complete motion cycle). Consequently, the number of sequences 215 can roughly match the number of stride actually completed by the runner during the run or other recording period. In some embodiments, it may not be necessary to have an exact match. Instead, the stride movement may simply provide a convenient, repeating pattern to capture.

Once stride extraction has been accomplished, producing an array of sequences in some embodiments, running gait metrics can be obtained by performing operations on each of the sequences by left/right sorting component 216, stride rate component 218, contact time component 220, acceleration component 222, and pelvic rotation component 224.

The stride metrics 208 can be provided to the user on display 210. Stride metrics 208 may be presented in one or more of text format, in a time-series graph, as a colored graph overlaid on a map, as haptic (vibrating) or audio feedback. In some embodiments, the display of data may occur in real time. The stride metrics output may formatted for a variety of mobile devices (represented at 226), presentation over the web (represented at 228), presentation to a thick client or otherwise.

Figure 3:
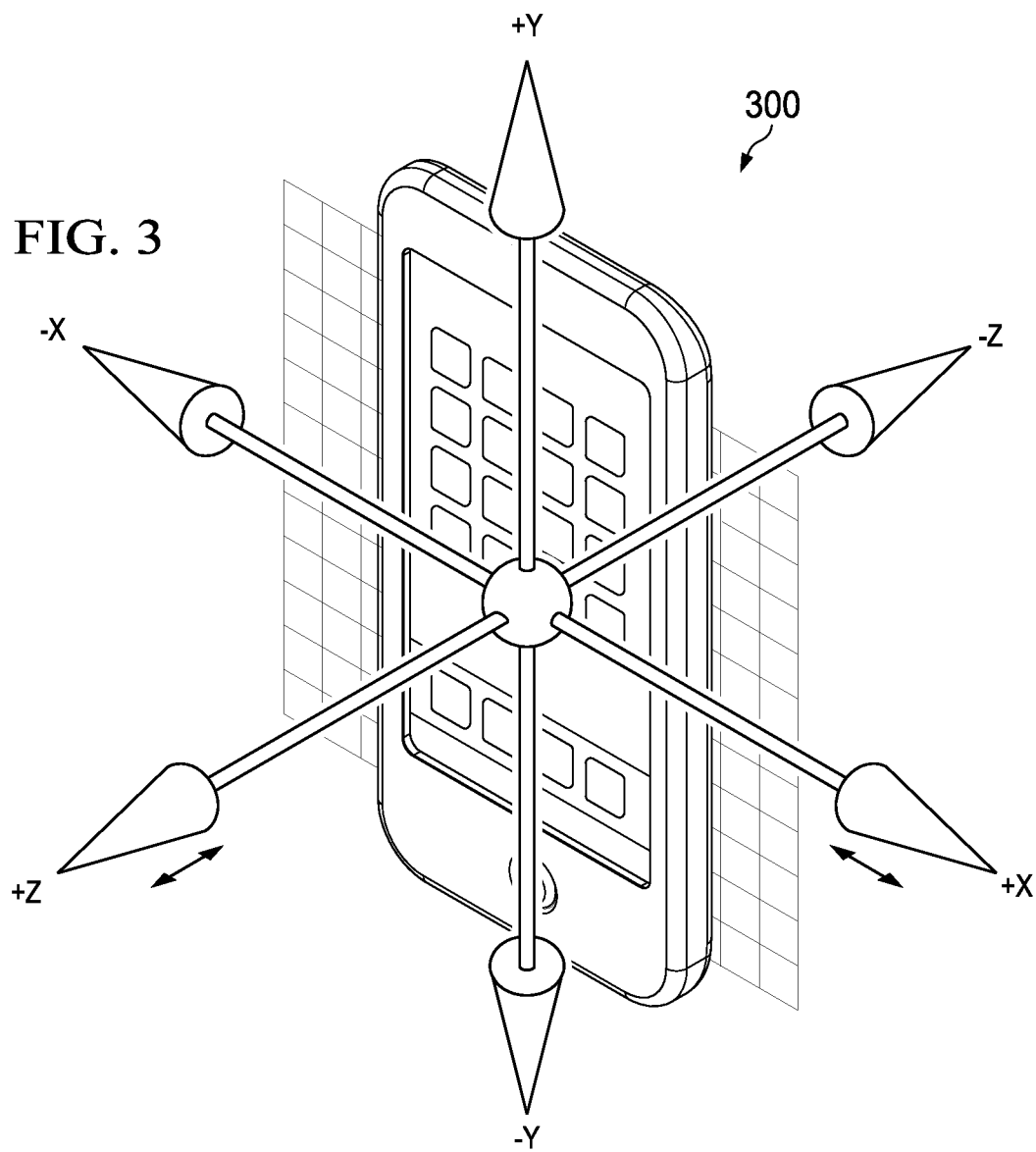
FIG. 3 illustrates accelerometer axes for use in embodiments.

Referring to FIG. 3, FIG. 3 depicts an embodiment of a data recording device 300 that contains an accelerometer and can be used as a data recording device 102 of FIG. 1. The alignment of the accelerometer determines which axis represents the vertical, lateral, and longitudinal acceleration. Depending on the orientation of the data recording device 300, the accelerometer may measure vertical, lateral, or longitudinal acceleration on any of the axes.

Figure 4:
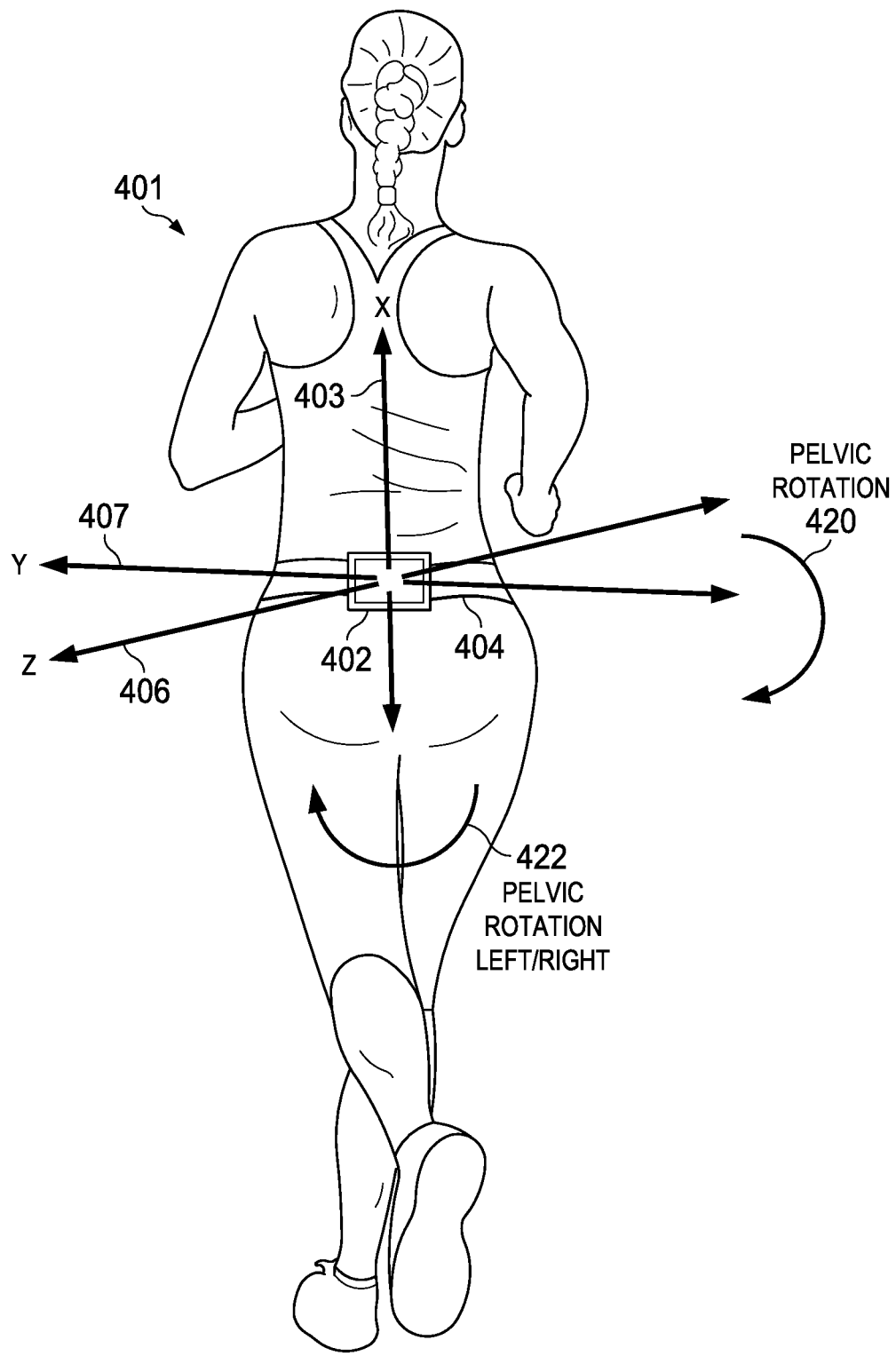
FIG. 4 illustrates device positioning according to embodiments.

FIG. 4 depicts one embodiment of a smartphone 402 that can be worn by a user 401 on a harness 404. Smartphone 402 can be an embodiment of a data recording device 102 (FIG. 1). Smartphone 402 may include an accelerometer that measures acceleration along an x-axis 403, y-axis 407, and z-axis 406. In the orientation illustrated, the x-axis corresponds to lateral acceleration and the z-axis to longitudinal acceleration. The accelerometer may be otherwise oriented, however.

During running, the human body exhibits complex motion, including limb movement and pelvic rotation about both the vertical and horizontal axes of the runner. To reduce the influence of these motions of accelerometer data, the accelerometer of smartphone 402 (or other data recording device) can be located close to the user's vertical centerline. By way of example, but not limitation, the accelerometer may be placed at the base of the user's spine. In the embodiment of FIG. 4, for example, smartphone 402 is carried in a harness 404 so that the accelerometer is located at the base of the user's spine. In other embodiments, smartphone 402 (or other data recording device) may be placed elsewhere on the body, such as worn on a shoe or carried by hand.

Returning to FIG. 2, as noted above, process flow may start with data recording 202. This process occurs while the user is running and may start and end by the user pressing a hardware or software button on the data recording device (e.g., data recording device 102 of FIG. 1) or at the occurrence of other defined events.

A simple way to capture this data is by capturing all of the sensors simultaneously (or close enough to simultaneously so that the time differences are functionally negligible). These sensors can include, but are not limited to: acceleration, rotation GPS, altitude, magnetometer. According to one embodiment, the data can be recorded as follows in Table 1:

TABLE 1

| time | $acceleration_x$ | $acceleration_y$ | $acceleration_z$ | roll | pitch | $GPS_{latitude}$ | $GPS_{longitude}$ |
|---|---|---|---|---|---|---|---|
| 0.010 | 1.1274 | 0.037373 | 0.2363456 | 17.1764 | 34.4766 | 97.0737 | 35.0745 |
| 0.020 | 1.2636 | 0.037654 | 0.2745674 | 17.16544 | 34.497 | 97.0734 | 35.0764 |
| 0.030 | 1.6356 | 0.0298765 | 0.2745675 | 17.1867 | 34.4764 | 97.0764 | 35.0746 |

TABLE 1-continued

| time | acceleration$_x$ | acceleration$_y$ | acceleration$_z$ | roll | pitch | GPS$_{latitude}$ | GPS$_{longitude}$ |
|---|---|---|---|---|---|---|---|
| 0.040 | 1.6358 | 0.035434 | 0.24567764 | 17.1574 | 34.4726 | 97.0764 | 35.0764 |
| 0.050 | 1.6354 | 0.039896 | 0.2457645 | 17.17476 | 34.4653 | 97.0888 | 35.0746 |

In the example of Table 1, a 100 sample/second frequency is used. However, any suitable sampling frequency may be employed. Additionally, Table 1 is provided by way of example, not limitation, and other types of data may be collected and various portions of data in Table 1 may be omitted.

An alternative to a single sample rate design is to record each type of data at a rate that captures the likely changes of that variable, which varies depending on the desired resolution of particular measures. GPS data, for example, is rarely updated on a receiver at rates much over 1 Hz, which may make sampling at 100 Hz redundant. On the other hand, since contact time is typically computed entirely in the time-domain, higher resolution data contributes directly to higher resolution contact time measurement.

Data processing component 206 transforms the raw sensor data 204. As noted above, processing component 206 may include a normalization component 212 to normalize raw data 204. This may include standardizing the frame of reference, standardizing the units and compensation for improper placement of the data recording device, or other normalization.

Frame of reference normalization occurs because the accelerometer typically has a frame of reference relative to the data recording device. While the stride metrics (contact time, stride rate, acceleration, etc.) can be useful when computed from raw data that has a frame of reference (a set of basis vectors) relative to the data recording device, it may be desirable to transform the acceleration data into a coordinate system relative to the ground. This is adequate for the typical runner, whose primary intended use of stride metric data is to compare values from runs at different times (often across months or years) in order to gauge progress in efficiency or technique. It may be desirable to compare stride metrics across multiple users at a much higher level of precision (e.g., for scientific research purposes). In that case, it may be useful to change the frame of reference to one that is independent of a particular user's posture or device placement.

Some accelerometers provide a computation of the acceleration force due to gravity (a unit length vector that points in the direction of the ground). Gram-Schmidt orthonormalization or other normalization may be used to change the basis of the accelerometer data to a new frame of reference. Alternatively, Gram-Schmidt or other normalization can be used on an estimation of the gravity vector, which may be produced through other mechanism, such as a Kalman filter, hidden Markov model, or other machine-learning algorithm.

Units normalization may be needed because different operating systems or other applications that provide sensor data may provide the data in different formats. For example, digitized acceleration data is often expressed in terms of meters/second/second or in terms of g (9.8 meters/second/second) or in terms of the calibrated resolution range of the analog to digital converter, integers, i.e., 0-255 for an 8-bit system. According to one embodiment, data can be converted into a standard unit (for acceleration, this can be G, meters per second squared, or other acceleration unit). In addition, it may be necessary to infer the units from the sensor data itself. For example, in the example above, assuming the data will be from an accelerometer that truncates values above 2 Gs, the data may range between (−20,20) (m/s/s), (−2,2 (g), (0-255 (integers), etc. depending on the units used by the sensor).

Placement compensation can be applied because in some cases the accelerometer may be placed in the wrong orientation or position. For example, data might be collected with the data recording device flipped upside-down. This can be detected because the mean x-axis accelerometer data will be negative rather than positive. If so, the sign of all relevant data (x-axis acceleration, y-axis acceleration, x & y rotation) can be flipped. Similarly, orientation may be determined based on the magnitude of readings along each axis as the vertical axis will generally exhibit the largest magnitude readings. Thus, if the z-axis is associated with the largest magnitude acceleration readings, largest magnitude regularly repeating acceleration readings, or acceleration readings meeting other criteria, this can indicate that the z-axis is the vertical axis.

Stride extraction component 214 processes a set of sensor data (in some cases, normalized data or otherwise pre-processed sensor data) to identify data corresponding to strides. One embodiment of stride extraction is discussed in conjunction with FIGS. 5A, 5B and 6. The results of stride extraction component 214 can be used by left/right sorting component 216, stride rate component 218, contact time component 220, acceleration component 222 and pelvic rotation component 224 to provide stride metrics. Embodiments of left/right sorting and contact time determination are discussed below in conjunction with FIG. 6. One embodiment of determining acceleration is discussed in conjunction with FIG. 7.

Figure 5A:
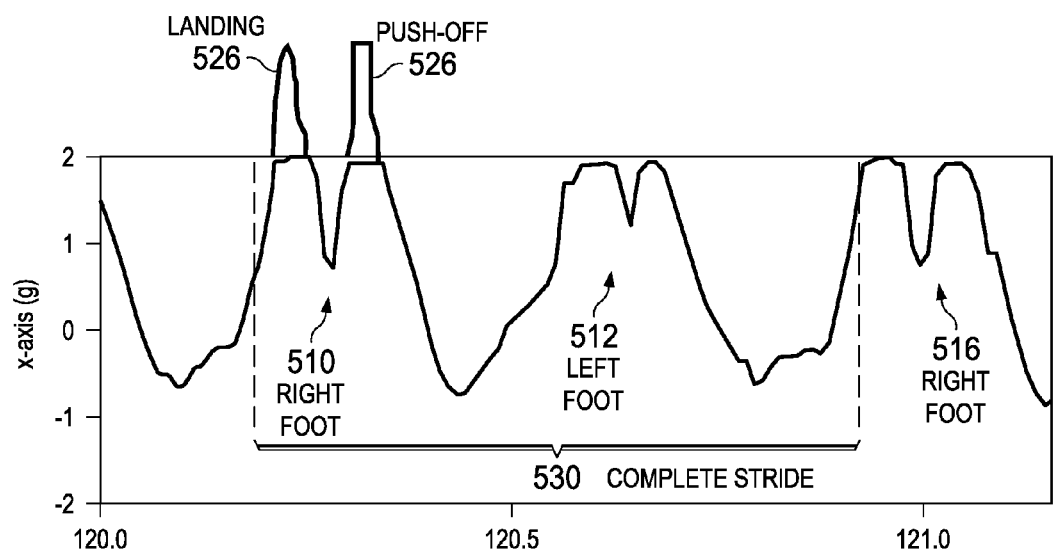
FIG. 5A illustrates the relationship between stride and vertical acceleration data according to embodiments.

FIG. 5A illustrates the relationship between stride and vertical acceleration data in greater detail. In the embodiment of FIG. 5A, it is assumed that the x-axis data corresponds to vertical acceleration. However, vertical acceleration may be represented on another axis of the accelerometer. As shown, x-axis accelerometer data is plotted versus time. Steps are shown at 510, 512, and 514, representative of, for example, right, left, and right foot steps, respectively. A stride 530 comprises two steps.

Each step has a landing 526 and push off 528. Typically, the greatest vertical acceleration occurs at landing 526 and push off 528. However, some accelerometers, have a limit on the magnitude of acceleration that can be measured and thus the full acceleration associated with a step is not completely measured. As shown in FIG. 5A, for example, an accelerometer with a 2 G limit will cut-off landing 526 and push off 528.

Figure 5B:
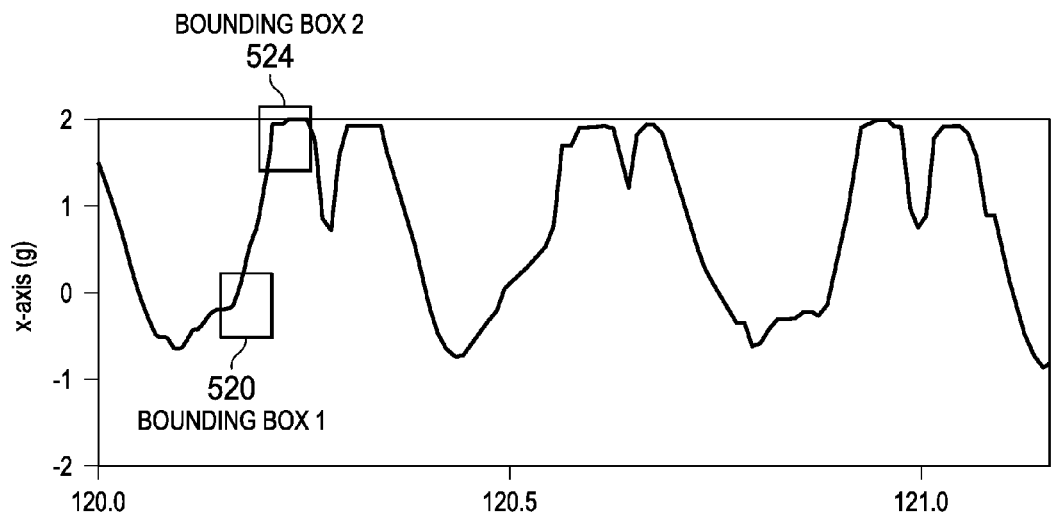
FIG. 5B illustrates a time series graph of x-axis accelerometer data and use of bounding boxes according to embodiments.

FIG. 5B is a time-series graph of X-axis accelerometer data shown for approximately two seconds. Broadly speaking, 0 g's and below define when a runner is airborne. A rapid increase in acceleration defines a landing while a rapid decrease in the magnitude of acceleration represents a push-off. However, the rapid increase in acceleration associated with a landing and the rapid decrease in acceleration associated with a push-off may have to be differentiated from increases and decreases in acceleration experienced as the user's foot transitions from landing to push off (represented at 529).

One embodiment of stride extraction uses a series of thresholds, both in time and amplitude that are set relative to data points of vertical acceleration data. Specifically, if one chooses a single data point and then finds that other points of data exist in "bounding boxes" (sections of time and acceleration, e.g., 520, 524) relative to that initial data point, one can conclude with reasonable certainty that a stride occurred during the time directly following the time of that data point. If one performs this analysis on each data point (or a sufficient number of data points) of vertical acceleration data that occurred during a run, and records the data points that meet this criterion, one has an approximate measure of the number of strides that occurred.

The placement of bounding boxes according to an embodiment follows a general plan that if there is a data point at time t1 then there must be a data point at time t2 having a vertical acceleration of a2, where:

$$t1+c \leq t2 \leq t1+j \text{ and } m \leq a2 \leq n; \text{ and}$$

a data point at time t3 having a vertical acceleration a3, where $$t1+k \leq t3 \leq t1+l \text{ and } p \leq a3 \leq q, \text{ where}$$

c=first time offset
j=second time offset
k=third time offset
l=fourth time offset
m=first bounding box lower acceleration limit
n=first bounding box upper acceleration limit
p=second bounding box lower acceleration limit
q=second bounding box upper acceleration limit The values of j, k, l, m, n, p, and q can be determined through empirical testing or other process. For an accelerometer with an acceleration limit, m, n, and p are preferably below that limit, while q may be below the limit or above the limit.

According to an embodiment, for example, the bounding boxes can be set such that:

If there is a data point (t1, a1), and the following data points:

data point ((t1+0.0 to 0.3 seconds), 0-0.3 (g)) (bounding box 1 520); and data point ((t1+0.1 to 0.5 seconds), 1.8-2.1 (g)) (bounding box 2 524)

the start of a new stride is identified. (It can be noted however, multiple data points in the same bounding box meeting the criteria are not considered to indicate new strides. For example, two data points in the same bounding box meeting the criteria above are not considered indicate the start of different strides).

These particular values for the bounding boxes are known to work from empirical testing. Other embodiments of bounding boxes can also be used to detect an event indicative of a stride in the data pattern. For example, the time and g limits of the bounding boxes may be adjusted. Moreover, other thresholding techniques can be used to detect strides.

Once a sequence of vertical acceleration data is identified as meeting the stride extraction criteria, that sequence is stored. For example, once it is determined that a set of data meets the criteria of bounding box 520 and bounding box 524, discussed above, the sequence of data is stored for that event. The length of the sequence should have enough data to record a complete stride. Since most people run at over 120 strides per minute, collecting ½ a second of data in each sequence is a reasonable rule of thumb. According to one embodiment, a sequence may be stored in an array of sequences, each sequence having the same length. In other embodiments, sequences may have different lengths. Sequences may also be stored in other data structures.

FIG. 6 depicts one embodiment of x-axis accelerometer data 602, y-axis accelerometer data 604, and z-axis accelerometer data 606 using the orientation of axes illustrated in FIG. 4. Using the bounding boxes discussed above in conjunction with FIG. 5B, the beginning of strides can be identified at 606 and 608 (additional strides can also be identified). Sequence data in time window 610 can be recorded for the first stride and sequence data in time window 612 can be recorded for the second stride. It can be noted that in this example the sequences can include overlapping data. In addition, parallel sequences in other data sets (e.g., other accelerometer data, gyroscope data, etc.) can be recorded into similar arrays (corresponding to the same time) or other data structures.

While the vertical acceleration data is used for stride extraction, identification of which leg (left or right) started each stride (stride sorting 216) primarily involves the lateral acceleration data (e.g., y-axis acceleration data using the orientation of FIG. 4), as shown for example, at 604 in FIG. 6. While the x-axis data can be nearly identical for left and right strides, the y-axis data will be in opposite directions in magnitude. Thus, the y component of the sequence is used for determining which leg was involved with each stride. For example, as shown in graph 604 of FIG. 6, the y-axis waveform at 612 is opposite in magnitude from 613. The wave at those points, either singly or in combination with the x-axis data 602, can be used to determine a left-right distinction.

In one embodiment, left/right sorting is done after the workout is finished. A cluster analysis method, such as k-means or other cluster analysis method, can be utilized to separate the sequences of y-axis data into two groups fairly easily since these sequences, expressed as vectors, will not overlap in the high dimensional space. However, this is only true if the strides themselves vary only slightly in their rate, which is common for many runners.

In situations where this is not the case, these sequences can be converted into a format which will make them easily separable by clustering methods. One way to do this is to choose a common event, such as a second time being airborne in a sequence, as determined by the x-axis data (e.g., using a bounding box, other thresholding, or other mechanism), and "stretch" the sequences so that each digital vector will end at this event. The sequences are interpolated (e.g., using an interpolation algorithm with a uniform sequence of points) so that the sequences for a user will have equal length and starting and ending events.

To provide an example, it is known that a user experiences 0 g at certain points in the stride (e.g., when the user is in the air). Therefore a threshold can be set to identify when the user is in the air. Threshold 628 can be set at 0 g (or other acceleration). When the acceleration data crosses the threshold (drops below threshold 628 when data in a sequence was previously above 628), it can be determined that the runner is in the air. The second time the event occurs in a sequence can be identified as a stretching event.

Using the example of FIG. 6, when the vertical acceleration of the first vertical acceleration data sequence crosses threshold 628 at event 630, this can be identified at the stretching event of the first set of sequences (the data sequences corresponding to the first time window 610) and when the second vertical acceleration sequence (data sequences corresponding to second time window 612) crosses threshold 628 at event 640, this can be identified as the stretching event of the second set of sequences.

The first lateral acceleration sequence corresponding to the first time window 610 can be stretched to the time of event 630 and the second lateral acceleration sequences corresponding to the second time window 612 can be stretched to the time of event 640. Thus, while the sequences may vary in time, they can be stretched to a common set of events to allow application of clustering algorithms. It can be noted that other events and methods of identifying events can be used.

Left/right sorting can be done in real-time (e.g., on the recording device, a server, or other device). Many clustering methods (such as k-means) produce template or prototype sequences, so that real-time left/right identification of sequences can be obtained by computing the RMS (root mean-square) error or other goodness of fit measure against each template, and choosing the template (left/right) with the least error (best goodness of fit). Alternatively, in another embodiment, a maximum RMS error (or other threshold) can be set, so that sequences exhibiting too high an error (too low a goodness of fit) may be left undetermined.

To determine stride rate, the periodicity of a sequence may be analyzed. One way to determine the main periodicity of each sequence is to compute the Fourier transform of the autocorrelation of the sequence, and then find the frequency that contains the most power. This frequency, expressed as Hz, can by multiplied by 60 to give the strides per minute. For example, the Fourier transform can be applied to each x-axis sequence to determine the strides per minute at the various times in a run.

While in the embodiment discussed above, the stride rate is determined from stride sequences, the stride rate may also be determined from other data sets. Provided that the data set to which the transform is applied is long enough, the average stride periodicity can be extracted from any length of digital data including the entire raw sensor data stream or portion thereof. Computing the stride frequency in this manner is invariant to the placement of the accelerometer.

To measure the time that each foot was on the ground, a finite-length threshold method may be used on each sequence. Such a threshold is illustrated, for example, at 641 in FIG. 6, which defines a threshold at 1.8 gs, though other thresholds can be used. In operation, one embodiment can 1) find all acceleration values above 1.8 (g) and between upper and lower time boundaries (e.g., 0 and 0.5 seconds after the sequence start or other time boundaries); and 2) take the time difference between the first and last in the group. For example, the time between event 642 and event 644 represent an estimation of the contact time for a foot.

This estimation may be proportional the actual time the foot is on the ground. The proportion constant can be found by comparing this method with direct measures, such as a treadmill that measures ground forces. Asymmetry in contact time can be computed by finding the difference in contact time across successive strides.

Figure 7:
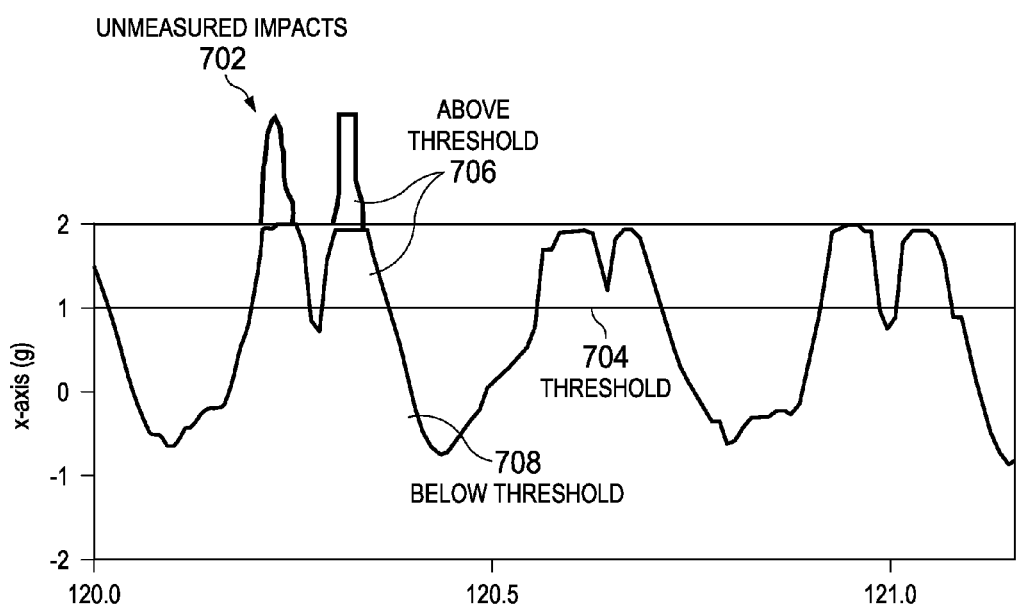
FIG. 7 illustrates determination of an acceleration metric.

Determination of acceleration is shown with reference to FIG. 7. It may be recalled that some accelerometers lack sufficient range to record the entire acceleration range of a runner. One embodiment can provide an estimate of maximum acceleration. Summary measures of acceleration for each stride are valuable to the runner as they are inversely correlated with efficiency and positively correlated with increased joint stress and injury. However, many of the critical accelerations cannot be directly measured because of the limitation of measurement of the accelerometer. For the example of FIG. 7, the accelerometer clips acceleration data at 2 g. Therefore the highest acceleration remains unmeasured (as represented by 702).

One method to find a measure of vertical acceleration is to assume that the amount of momentum in the vertical direction is a constant. A threshold 704 can be defined. This defines a threshold 704 by which, according to the impulse momentum theorem, the sum of the accelerations will be zero if one defines all above the threshold 706 as positive values and all the values below as negative 708. That is, the area above the threshold 704 should be equal to the area below the threshold 708. In the example given, the threshold is set to 1 g, though other threshold under the accelerometers limit may be used.

The measurable area above threshold 704 and area below threshold 704 for a stride can be determined. The unmeasured area 702 above the accelerometer limit can be found based on the difference between the area below the threshold 708 and the measurable area above the threshold 706. While the extracted measure does not give greatest absolute magnitude of the acceleration, it does give a value that the runner can control, and will be highly correlated with the absolute magnitude. To find an independent measure of vertical momentum, altitude measurements (from global positioning systems or altimeters) can be used.

Horizontal (forward and backwards) and lateral accelerations are unlikely to be more than 2 gs (which is below the limit of many accelerometers) and given a symmetrical stride, are likely to be symmetrical. Metrics such as the maximum or average absolute horizontal and lateral acceleration, differences in successive strides and other metrics may be determined.

Pelvic rotation is rotation about a lateral and vertical axis (FIG. 4) and can be measured by a gyroscope. However, since this measurement is about the axis of the gyroscope, it will not directly measure the amount of pelvic rotation about axes centered in the pelvis. For the purposes of measuring the relative amounts of rotation amongst people who are all wearing the same type of data recording device containing the gyroscope, summary measures, such as the absolute magnitude, the average/sequence, and measures of asymmetry, are sufficiently useful. However, these measures will be proportional to those about pelvic centers. The proportionality can be measured from empirical observation and testing of pelvic rotations such that the measured rotation can be correlated to an absolute magnitude.

Figure 8:
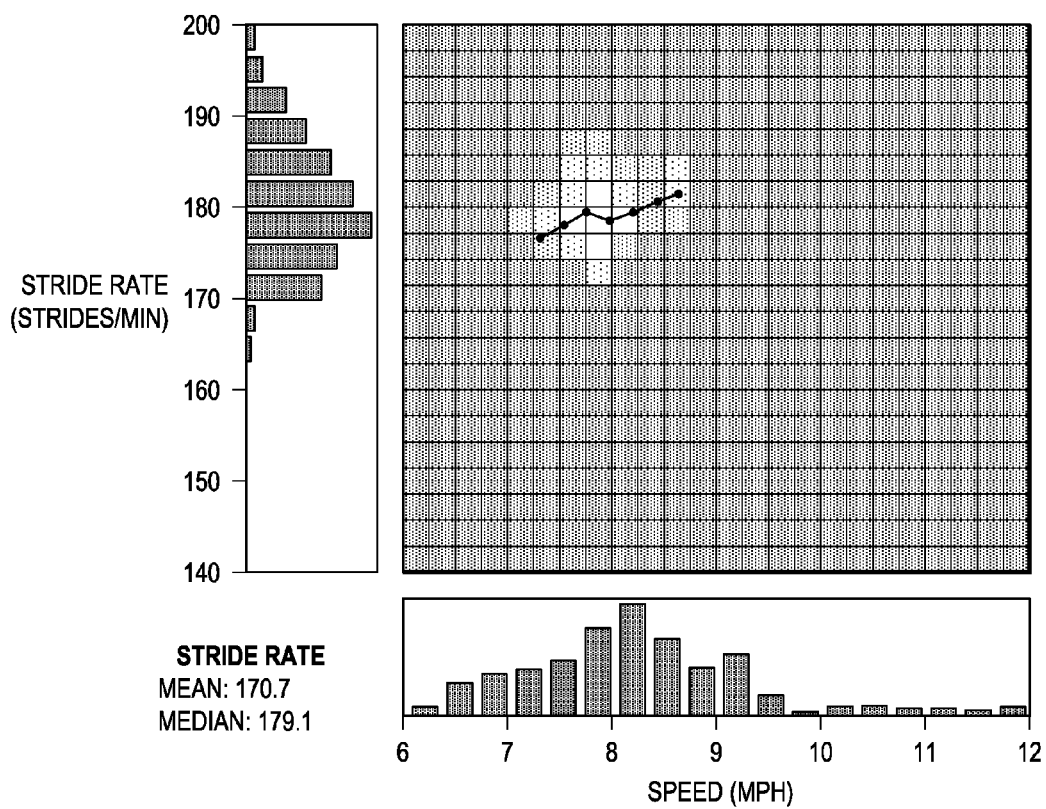
FIG. 8 illustrates a graphical user interface for presenting gait analysis data.

Data may be displayed through a variety of mechanisms. One option is to make various statistical plots of the data, expressing the distribution of the statistic or the relationship between one or more statistics. Information displayed may include pace, stride rate, contact time, vertical acceleration measure, elevation change, lateral acceleration, horizontal (forward/backward) acceleration and other metrics. Various metrics may be compared. For example, as shown in FIG. 8, stride rate and speed may be plotted, showing the relationship. As another example, a chart or other representation of elevation and pace can be provided. As yet another example, plots of stride times, lateral accelerations and measures of vertical accelerations can be provided, in some cases, with data points for left and right strides differentiated.

Furthermore, various metrics can be qualitatively classified to provide insight as to whether the runner is exhibiting desired running characteristics. For example, the display can show whether contact time, stride rate, pace or other characteristic is classified as "good", "acceptable", "bad" or has another classification. The classifications may be relative to the individual runner or be based on analysis of multiple runners.

Figure 9:
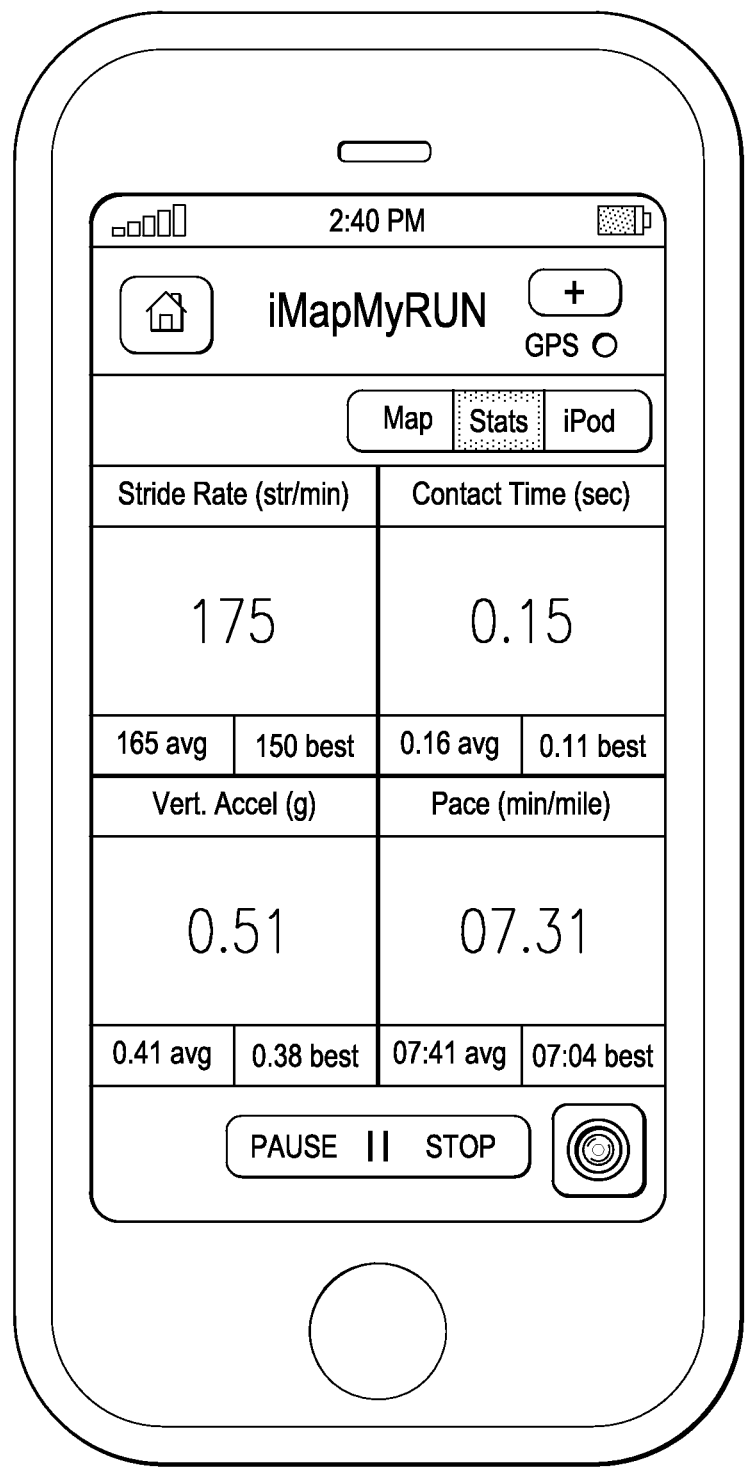
FIG. 9 illustrates a graphical user interface for presenting gait analysis data.

According to other embodiments, a user interface may display data while a workout is ongoing. FIG. 9 is a diagram illustrating an example user interface for displaying data while the user is completing the workout. As shown, metrics such as stride rate, contact time, vertical acceleration, and pace may be displayed. In other embodiments, other or additional metrics may be displayed.

Another display option includes aural information through headphones or speaker. One option is for an automated message to played from the data recording device, where the message played can be selected based on a particular metric. Alternatively, a live coach can give real time feedback. Haptic feedback can be given through vibration.

Figure 10:
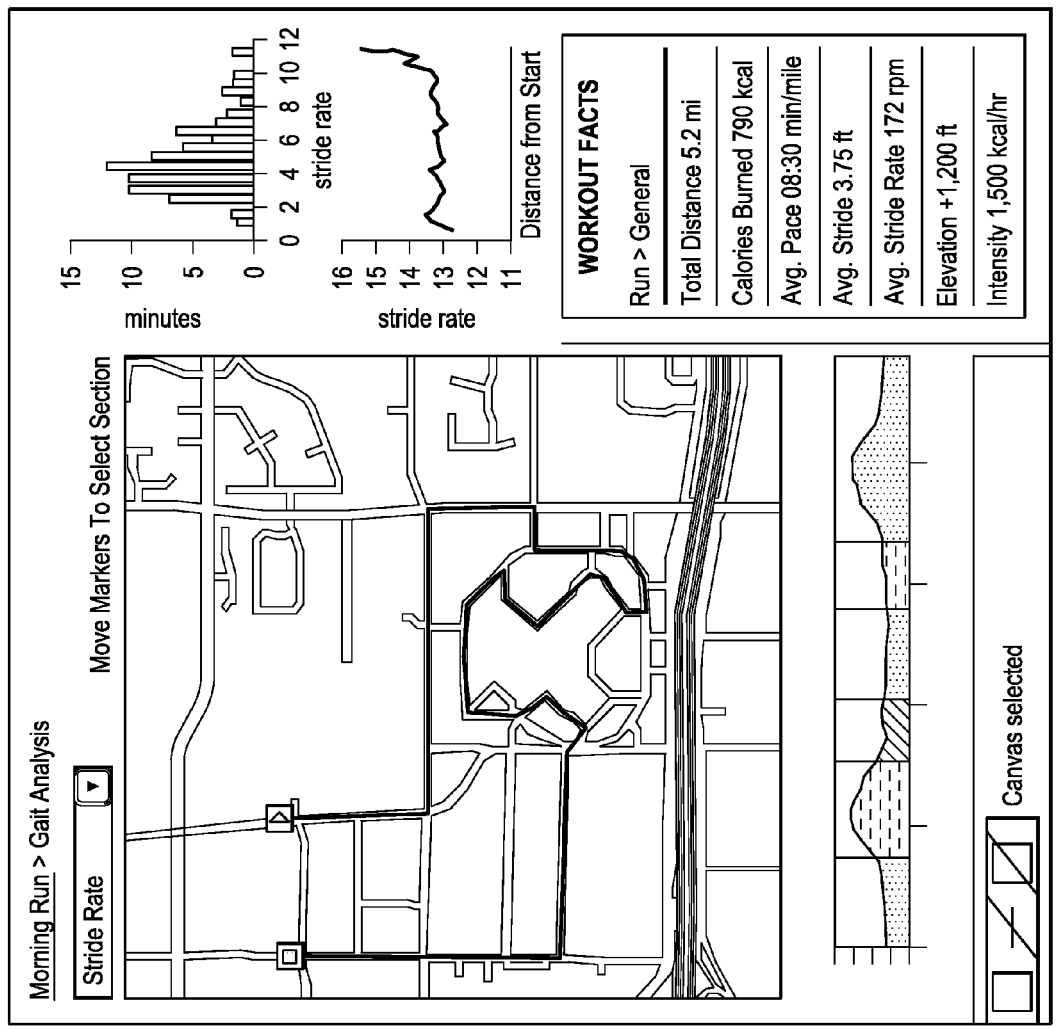
FIG. 10 illustrates a graphical user interface including a map for presenting gait analysis data.

According to one embodiment, stride metrics can be displayed on a map of the route the user took during the workout. This data may be smoothed. An example map and associated workout data are shown in FIG. 10. In the example illustrated, a map of the turn, one or more data plots, and a workout summary are shown. Color coding or other indications may be used to visually depict stride rate, pace and other metrics for different portions of the route. It is noted that, depending on the embodiments, other or different associated data may be displayed.

Figure 11:
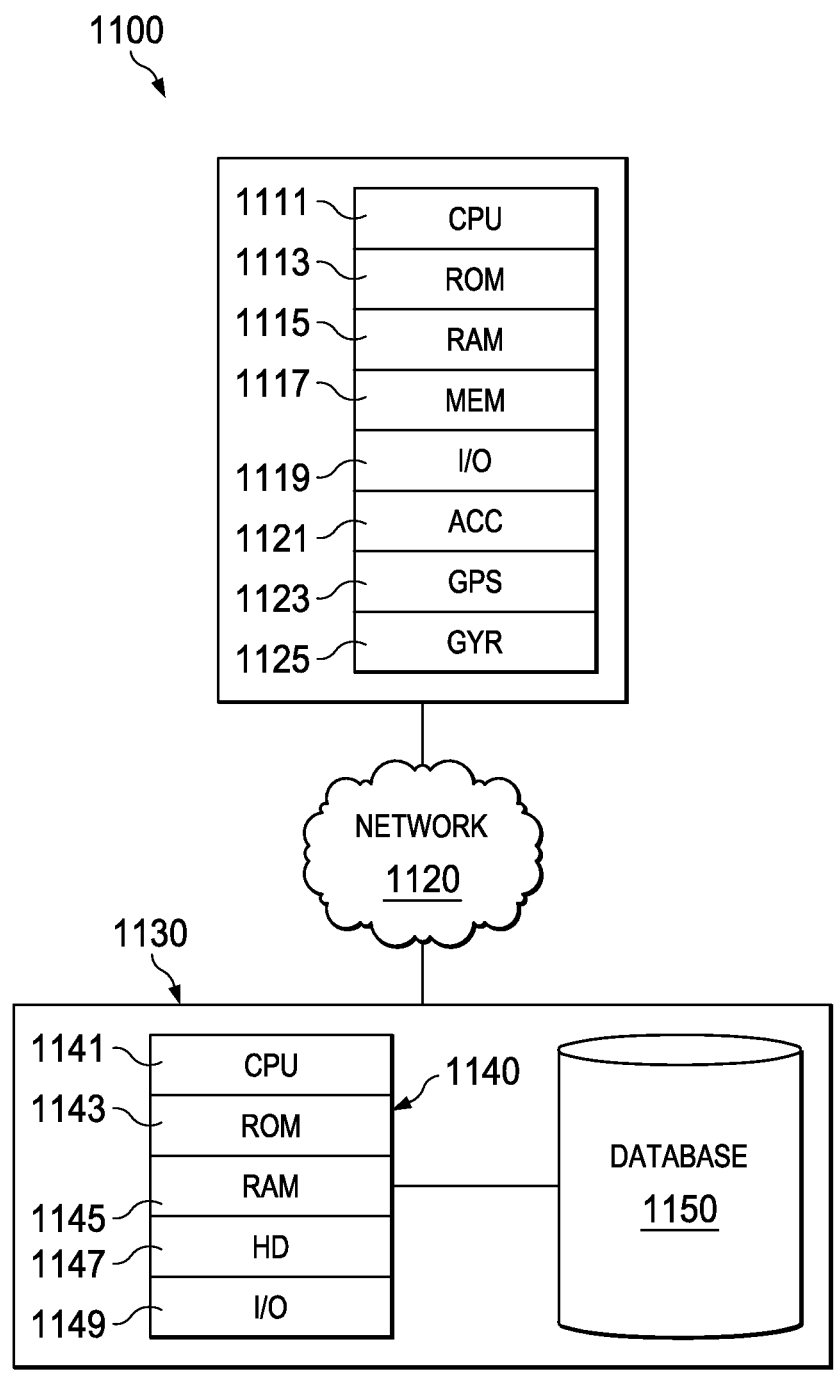
FIG. 11 illustrates an exemplary network computing environment in accordance with embodiments.

Referring to FIG. 11, one embodiment of a computer architecture is illustrated. The client and server computers and data source represent an exemplary hardware configuration of data processing systems that are capable of bi-directionally communicating with each other over a public network such as the Internet. Those skilled in the art will appreciate that network computing environment 1100 may comprise multiple server computers, and multiple client computers and data sources may be bi-directionally coupled to enterprise computing environment 1130 over network 1120.

Client computer 1110 can be one embodiment of a data recording device 102 and can include central processing unit ("CPU") 1111, read-only memory ("ROM") 1113, random access memory ("RAM") 1115, hard drive ("HD") or storage memory 1117, and input/output device(s) ("I/O") 1119. I/O 1119 can include a keyboard, display, etc. Examples of I/O 1119 may include mouse, touchscreen, trackball, stylus, or the like. Client computer 1110 may include sensor devices such as accelerometer 1121, GPS 1023, gyroscope 1025 and other sensors.

According to one embodiment client computer 1110 can be a smartphone providing an operating system and running one or more applications. According to one embodiment, the application may record data collected by one or more of the sensor devices and process the data as discussed above. In another embodiment, the application may pass the data to server 1140.

Server computer 1140 may have hardware components including CPU 1141, ROM 1143, RAM 1145, HD 1147, and I/O 1149. Server computer 1140 may execute programs to receive and process data from client computer 1110. Data may be stored in a database 1150, RAM 1145, HD 1147 or elsewhere.

Portions of the methods described herein may be implemented through execution of suitable software code that may reside within ROM 1113, 1143, RAM 1115, 1145, secondary storage 1117, 1147, database 1150 or other non-transitory computer readable medium accessible by processor 1111 or 11141. In some embodiments, computer instructions implementing an embodiment disclosed herein may be stored on a direct access storage device (DASD) array, magnetic tape, floppy diskette, optical storage device, or other appropriate computer-readable storage medium or storage device. A computer program product implementing an embodiment disclosed herein may therefore comprise one or more non-transitory computer readable media storing computer instructions translatable by CPU 1141 or CPU 1111 to perform an embodiment of a method disclosed herein.

Other architectures may be used. For example, the functions of server computer 1140 may be distributed and performed by multiple computers in enterprise computing environment 1130 or in a cloud in network computing environment 1100. Similarly, the functions of computer 1110 may be distributed and performed by multiple computers. Accordingly, each of the computer-readable storage media storing computer instructions implementing an embodiment disclosed herein may reside on or accessible by one or more client computers and computers in enterprise computing environment 1130 or in a cloud in network computing environment 1100.

As noted above, a harness can be used to ensure that the accelerometer readings occur at a symmetrical position at the center of the back and bottom of the spine, preferably adjacent to the lumbar-sacral junction. Features of one embodiment of a harness 1204 are illustrated more particularly with reference to FIG. 12A and FIG. 12B.

In some embodiments, the mobile data recording device may be implemented as an Apple iPhone, Android phone, PDA, or other data processing device. In such embodiments, the harness 1204 puts the data recording device in an orientation with its longest axis positioned laterally across the back. In the Apple IOS, this orients the accelerometer 1223 (FIG. 12B) so that the x-axis is defined as roughly vertical when the harness 1204 is being worn and the user is standing/running, with positive and negative values representing up and down, respectively. Similarly, the y-axis is defined roughly laterally left-right (negative/positive), and the z-axis is roughly front-back (positive/negative). It is noted, however, that this axis is relative to the phone itself, and not the earth. In some cases, the axes may be switched.

Shown in FIG. 12A is a front view of a harness 1204 including an elastic band 1201, and a static cord 1203 affixed to a ratcheting buckle 1202. The ratcheting buckle 1102 secures the static cord 1203, ensuring the harness 1204 stays in position. The ratcheting buckle 1202 may further include a quick release 1206 for alignment.

As shown by rear view in FIG. 12B, the harness 1204 may include a phone case 1220 into which the data recording device may be inserted. The harness 1204 may further include a quick release buckle 1222 for easy removal. An example of an accelerometer location is shown at 1223. In some embodiments, normalization routines may account for the displacement from the body center.

It should be noted that, while the figures illustrate a particular implementation of a harness, any suitable mechanism for placing an accelerometer may be used. Further, in other embodiments, the accelerometer and/or other sensors may be placed elsewhere on the body depending on the metrics being determined and/or compensation processes employed.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary.

While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Any suitable programming language can be used to implement the routines, methods or programs of embodiments of the invention described herein, including C, C++, Java, assembly language, etc. Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or code steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more digital computers, by using application specific integrated circuits, programmable logic devices, field programmable gate arrays, optical, chemical, biological, quantum or nanoengineered systems, components and mechanisms may be used. For example, distributed, or networked systems, components and circuits can be used. In another example, communication or transfer (or otherwise moving from one place to another) of data may be wired, wireless, or by any other means.

A "computer-readable medium" may be any medium that can store code for use by or in connection with the instruction execution system, apparatus, system or device. The computer readable medium can be, by way of example only but not by limitation, an electronic, magnetic, optical, electromagnetic, or semiconductor system, apparatus, system, device, or computer memory. Such computer-readable medium shall generally be machine readable and can include software programming or code that can be human readable (e.g., source code) or machine readable (e.g., object code).

A "processor" includes any, hardware system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/Figures should be considered only as exemplary, and not limiting, unless otherwise specifically noted.

Furthermore, the term "or" as used herein is generally intended to mean "and/or" unless otherwise indicated. As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein and throughout the claims that follow, the meaning of "in" includes "in" and "on" unless the context clearly dictates otherwise. The scope of the present disclosure should be determined by the following claims and their legal equivalents.

Although the foregoing specification describes specific embodiments, numerous changes in the details of the embodiments disclosed herein and additional embodiments will be apparent to, and may be made by, persons of ordinary skill in the art having reference to this description. In this context, the specification and figures are to be regarded in an illustrative rather than a restrictive sense, and all such modifications are intended to be included within the scope of this disclosure. Accordingly, the scope of the present disclosure should be determined by the following claims and their legal equivalents.

What is claimed is:

1. A system for gait analysis comprising:
a mobile data recording device comprising an accelerometer, the data recording device configured to record accelerations associated with user motion; and
a data processing device in communication with the mobile data recording device, the data processing device configured to:
receive acceleration data from the mobile data recording device;
normalize a frame of reference of the acceleration data to relative to a surface on which the user moves;
apply a placement compensation to the acceleration data to adjust for a placement of the mobile data recording device at a position other than directly centered at a base of the user's spine;
process the acceleration data to extract stride data sequences from the acceleration data, each of the stride data sequences comprising data for a corresponding stride; and
determine one or more stride metrics utilizing the stride data sequences;
wherein the stride metrics are utilized by the user to gage efficiency via comparison to previously attained stride metrics.

2. A system in accordance with claim 1, wherein at least one of the mobile data recording device and the data processing device comprises a smartphone.

3. A system in accordance with claim 2, wherein the accelerometer has a vertical acceleration limit such that vertical acceleration data for the user is not measured at or above the acceleration limit.

4. A system in accordance with claim 3, wherein the data processing device is further configured to estimate the vertical acceleration which was not measured via equalization of an area of a vertical acceleration curve above and below a predefined threshold.

5. The non-transitory computer readable medium of claim 4, wherein the act of estimation further comprises a determination of a measure correlated with maximum vertical acceleration from the stride data sequences based on a sum of accelerations above and below a threshold.

6. A system in accordance with claim 1, wherein the data processing device is further configured to utilize lateral acceleration data to left/right sort strides.

7. A system in accordance with claim 1, wherein the data processing device is further configured to provide the one or more stride metrics to the data recording device for display to the user in real time.

8. The system of claim 1, wherein the one or more stride metrics comprise at least one of: a stride rate, a measure correlated to maximum vertical acceleration, or contact time.

9. A method for gait analysis, comprising:
at a mobile data recording device comprising a sensor, recording acceleration data associated with a user's gait collected during a run; and
at a data processing device, processing the acceleration data, the processing comprising:
estimating acceleration values which exceed an acceleration limit of the mobile data recording device;
adjusting a frame of reference of the estimated and collected acceleration data relative to a surface on which the user moves;
extracting stride data sequences from the normalized acceleration data, each of the stride data sequences defining a stride of the run;
determining one or more stride metrics utilizing the stride data sequences; and
providing the one or more stride metrics for display on a display device;
wherein the display further comprises a display of previously determined stride metrics for the user in order to enable the user to gauge progress.

10. A method in accordance with claim 9, wherein the act of estimating further comprises determining a measure correlated with maximum vertical acceleration from the stride data sequences based on a sum of accelerations above and below a threshold.

11. A method in accordance with claim 9, further comprising sorting left and right strides based on lateral acceleration data.

12. A method in accordance with claim 9, further comprising, determining stride rate based on the stride data sequences.

13. A method in accordance with claim 9, further comprising, determining contact time based on the stride data sequences.

14. A method in accordance with claim 9, wherein at least one of the data recording device and the data processing device comprises a smartphone.

15. A method in accordance with claim 9, further comprising applying a placement compensation to the acceleration data to adjust for a placement of the mobile data recording device on the user.

16. A non-transitory computer readable medium comprising a plurality of instructions which are configured to, when executed by a processor:

receive acceleration data collected by a mobile data recording device worn by a user during traversal of a route;

extract stride data sequences from the acceleration data, each of the stride data sequences comprising data for a corresponding stride;

determine one or more stride metrics utilizing the stride data sequences at least one of the stride metrics comprising a quality identifier; and provide the one or more stride metrics for display on a map of the route by the data recording device;

wherein the display comprises a color-coded visual depiction of the quality identifier associated to each stride throughout traversal of the route; and wherein the display of the stride metric further enables the user to gauge efficiency via a review previously determined stride metrics.

17. The non-transitory computer readable medium of claim 16, wherein the mobile data recording device is incapable of recording acceleration above a given limit, and the plurality of instructions are further configured to, when executed, estimate a vertical acceleration which above the limit via equalization of an area of a vertical acceleration curve above and below a predefined threshold.

18. The non-transitory computer readable medium of claim 16, wherein at least one of the stride metrics comprises stride rate based on the stride data sequences.

19. The non-transitory computer readable medium of claim 16, wherein at least one of the stride metrics comprises contact time based on the stride data sequences.

20. The non-transitory computer readable medium of claim 16, wherein the extraction of stride data sequences from the acceleration data comprises
normalization of a frame of reference of the acceleration data to relative to a surface on which the user moves.

21. The non-transitory computer readable medium of claim 16, wherein the extraction of stride data sequences from the acceleration data comprises application of a placement compensation to the acceleration data to adjust for a placement of the mobile data recording device on the user.

\* \* \* \* \*